United States Patent
Medema

(10) Patent No.: US 10,828,025 B2
(45) Date of Patent: Nov. 10, 2020

(54) SYSTEM AND METHOD FOR RAPID ATTACHMENT OF CARDIOVASCULAR PROSTHESIS

(71) Applicant: ON-X LIFE TECHNOLOGIES, INC., Austin, TX (US)

(72) Inventor: Ryan Medema, Plugerville, TX (US)

(73) Assignee: ON-X LIFE TECHNOLOGIES, INC., Austin, TX (US)

( * ) Notice: Subject to any disclaimer, the term of this patent is extended or adjusted under 35 U.S.C. 154(b) by 172 days.

(21) Appl. No.: 15/567,221

(22) PCT Filed: Apr. 16, 2016

(86) PCT No.: PCT/US2016/027999
§ 371 (c)(1),
(2) Date: Oct. 17, 2017

(87) PCT Pub. No.: WO2016/168775
PCT Pub. Date: Oct. 20, 2016

(65) Prior Publication Data
US 2018/0092638 A1   Apr. 5, 2018

Related U.S. Application Data

(60) Provisional application No. 62/148,962, filed on Apr. 17, 2015.

(51) Int. Cl.
*A61B 17/064* (2006.01)
*A61F 2/24* (2006.01)
*A61B 17/068* (2006.01)

(52) U.S. Cl.
CPC .......... *A61B 17/064* (2013.01); *A61B 17/068* (2013.01); *A61F 2/2409* (2013.01);
(Continued)

(58) Field of Classification Search
CPC ........ A61B 17/0401; A61B 2017/0409; A61B 2017/0427; A61B 2017/0412;
(Continued)

(56) References Cited

U.S. PATENT DOCUMENTS 5,342,376 A    8/1994   Ruff
6,966,916 B2   11/2005  Kumar
(Continued)

OTHER PUBLICATIONS

The International Searching Authority, "Notifaction of Transmittal of the International Search Report and the Written Opinion of the International Searching Authority", dated Jul. 22, 2016 in International Application No. PCT/US2016/027999.
(Continued)

*Primary Examiner* — Sarah A Simpson
(74) *Attorney, Agent, or Firm* — Trop, Pruner & Hu, P.C.

(57) ABSTRACT

An embodiment includes a system comprising: first and second conduits respectively including first and second barbed rods; first and second shafts; wherein: (a)(i) in a first configuration the first shaft slides distally within the first conduit and couples to a proximal end of the first barbed rod, and (a)(ii) in a second configuration the first shaft slides distally within the first conduit and pushes the first barbed rod out of the first conduit; wherein: (a)(i) in an additional first configuration the second shaft slides distally within the second conduit and couples to a proximal end of the second barbed rod, and (a)(ii) in an additional second configuration the second shaft slides distally within the second conduit and pushes the second barbed rod out of the second conduit. Other embodiments are described.

22 Claims, 9 Drawing Sheets

(52) U.S. Cl.
CPC .............. *A61B 2017/0647* (2013.01); *A61F 2220/0016* (2013.01); *A61F 2230/0097* (2013.01)

(58) Field of Classification Search
CPC ..... A61B 2017/0464; A61B 2017/0647; A61F 2/2442; A61F 2/2445; A61F 2/2409; A61F 2220/0016
See application file for complete search history.

(56) References Cited

U.S. PATENT DOCUMENTS

| | | |
|---|---|---|
| 7,197,362 B2 | 3/2007 | Westlund |
| 7,226,468 B2 | 6/2007 | Ruff |
| 8,277,502 B2 | 10/2012 | Miller et al. |
| 8,825,129 B2 | 9/2014 | Garcia et al. |
| 8,926,659 B2 | 1/2015 | Genova et al. |
| 9,044,225 B1* | 6/2015 | Goraltchouk .... A61B 17/06166 |
| 2006/0084943 A1 | 4/2006 | Rosenman et al. |
| 2013/0331930 A1* | 12/2013 | Rowe .................... A61F 2/2466 623/2.11 |
| 2014/0207154 A1 | 7/2014 | Bielefeld |
| 2016/0038280 A1* | 2/2016 | Morriss ................ A61F 2/2436 623/2.18 |

OTHER PUBLICATIONS

Watanabe et al, "Use of Barbed Suture in Robot-Assisted Mitral Valvuloplasty", 2015, pp. 343-345, The Society of Thoracic Surgeons.

Quill Device, "Quill: General Product information", Sep. 23, 2013, pp. 1-6, http://www.guilldevice.com/general-product-information.

Covidien, "Barbed Sutures: V-Loc Wound Closure Device—Covidien", 2015, pp. 1-2 http://www.covidien.com/surgical/products/wound-closure/barbed-sutures.

* cited by examiner

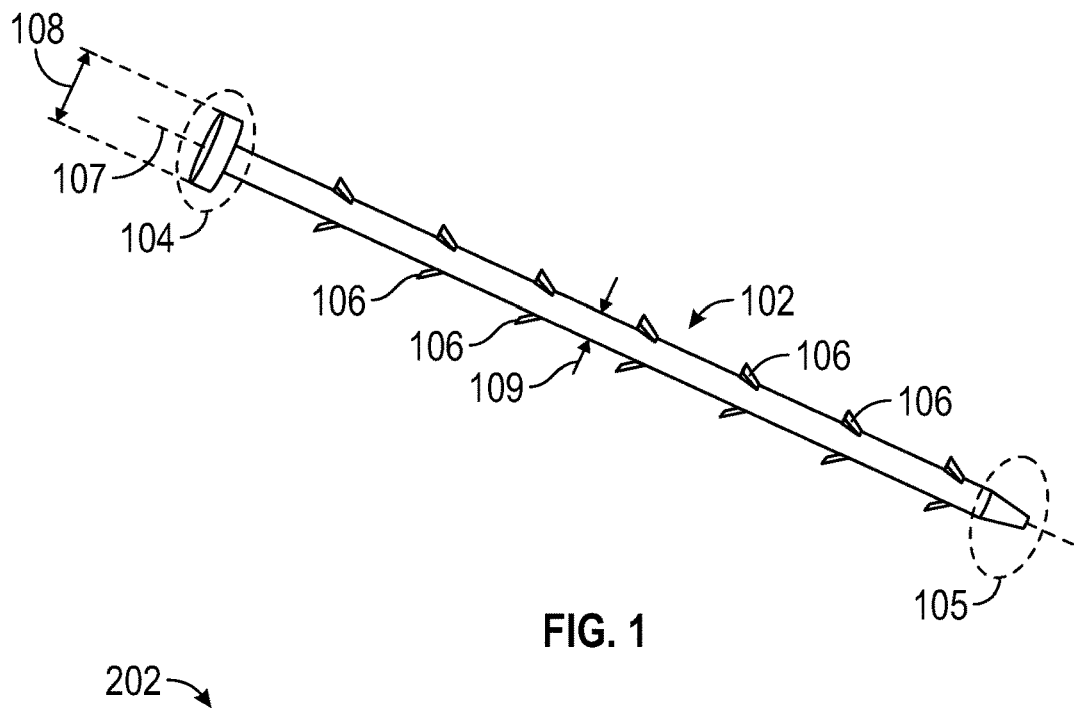
FIG. 1
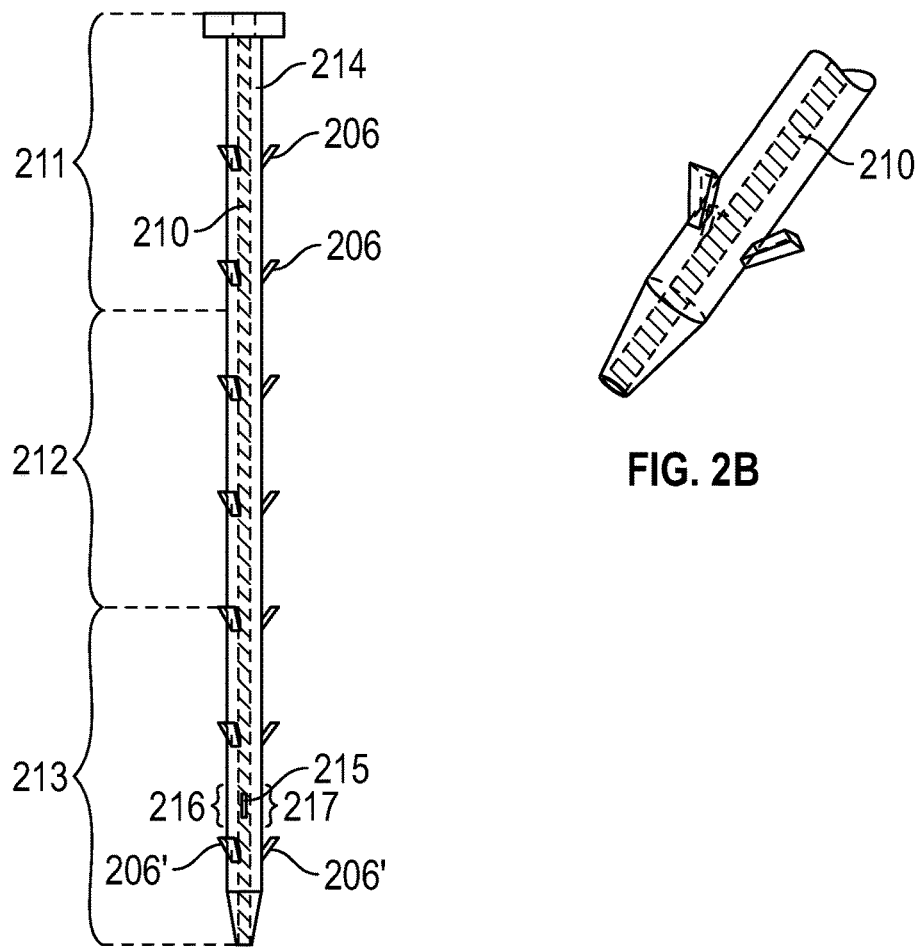
FIG. 2A
FIG. 2B

SYSTEM AND METHOD FOR RAPID ATTACHMENT OF CARDIOVASCULAR PROSTHESIS

PRIORITY CLAIM

This application claims priority to U.S. Provisional Patent Application No. 62/148,962 filed on Apr. 17, 2015 and entitled "System and Method for Rapid Attachment of Mechanical Heart Valve", the content of which is hereby incorporated by reference.

TECHNICAL FIELD

Embodiments of the invention are in the field of surgical coupling systems and, in particular, cardiovascular prosthesis coupling systems.

BACKGROUND

As addressed in *Prosthetic Aortic Valve Replacement* (Hans-Hinrich Seivers, Journal of Thoracic and Cardiovascular Surgery, 2005, Vol. 129: pp. 961-965), the aortic root includes segments of an ellipse where valve cusps are attached to the wall of the aorta and are supported by thickened, dense fibrous tissue. These fibrous thickenings form an "anatomic annulus" that has a crown-shaped configuration. The three elliptical portions of the crown confine the sinuses on one side as the most proximal part of the aorta and the intervalvular trigones on the other side, which at least hemodynamically belong to the left ventricle. The dense fibrous tissue of the "anatomic annulus" is strong and provides an anchor for suturing a prosthetic valve within the aortic root. A "basic annulus" consists of the nadirs of the elliptical attachments of the cusps, the septal muscle, the ventricular membranous septum, and the distal end of the aortomitral curtain, together termed sometimes the ventriculoarterial junction and defining the smallest cross-sectional area between the left ventricle and the aorta. As such, this "basic annulus" defines the width of the root as measured from the sizers and also the seating of the conventional circular prostheses because the prostheses are fixed with sutures through the nadirs of the annulus. A conventional implant technique seats the prosthetic valve along the annulus. The sewing ring of the valve is then sutured through the nadirs of the annulus.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIG. 1 depicts a prosthesis in an embodiment.
FIGS. 2a-2b depict a prosthesis in an embodiment.

DETAILED DESCRIPTION

Figure 3A:
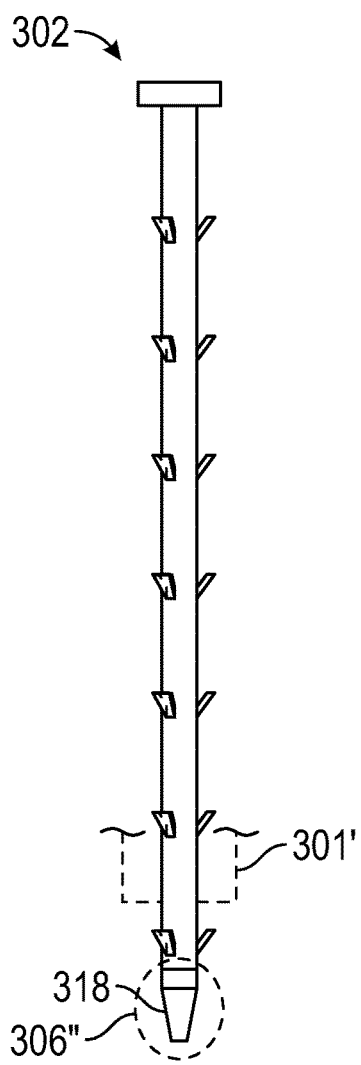
FIGS. 3a-3b depict a prosthesis in an embodiment.

In the following description, numerous specific details are set forth. However, it is understood that embodiments of the invention may be practiced without these specific details. Well-known structures and techniques have not been shown in detail to avoid obscuring an understanding of this description. References to "one embodiment", "an embodiment", "example embodiment", "various embodiments" and the like indicate the embodiment(s) so described may include particular features, structures, or characteristics, but not every embodiment necessarily includes the particular features, structures, or characteristics. Further, some embodiments may have some, all, or none of the features described for other embodiments. Also, as used herein "first", "second", "third" describe a common object and indicate that different instances of like objects are being referred to. Such adjectives are not intended to imply the objects so described must be in a given sequence, either temporally, spatially, in ranking, or in any other manner. Also, the terms "coupled" and "connected," along with their derivatives, may be used. In particular embodiments, "connected" may be used to indicate that two or more elements are in direct physical or electrical contact with each other and "coupled" may mean that two or more elements co-operate or interact with each other, but they may or may not be in direct physical or electrical contact. Also, while similar or same numbers may be used to designate same or similar parts in different figures, doing so does not mean all figures including similar or same numbers constitute a single or same embodiment.

A conventional method of attaching mechanical heart valves to cardiac tissue with needles/suture/pledgets is a difficult and time consuming process, which ultimately requires the patient to remain on a heart-lung bypass machine for an extended time. If the attachment of a valve were simplified and the attachment time was greatly reduced (as is the case with embodiments described herein), patients would rely on the heart/lung bypass machine for significantly less time, and would experience overall better surgical outcomes.

An embodiment provides rapid attachment of a cardiovascular prosthesis (e.g., mechanical heart valve) via a series of implantable spike-like prostheses, instead of using a conventional method that relies on needle, suture, and/or pledgets. The embodiment is knotless. However, in some embodiments a physician may choose to use traditional suture in combination with the spike-like prostheses.

An embodiment of the prosthesis spike, as fabricated from barbed suture, forms a permanent anchor to attach a mechanical heart valve to surrounding tissue. Several spikes together form a system of attachment which effectively replace or at least augment the conventional method of suturing and hand-tying the valve (e.g., mechanical or tissue) into position.

An embodiment includes locating a stiff core rod (e.g., metal, shape-memory alloy, polymer, plastic) within barbed suture. An embodiment includes locating a stiff core rod (e.g., metal or shape-memory alloy) within an outer layer of material (e.g., polypropylene, PTFE, ePTFE, and nylon) that has barbs formed thereon and that covers a majority of the stiff core.

In an embodiment a distal most portion of the stiff core rod is exposed beyond the outer covering to facilitate piercing a sewing ring and/or fibrous annulus. For example, in FIG. 3a no core is shown but tip 318 could be coupled to a core such as core 210 of FIG. 2a. However, in other embodiments tip 318 is not coupled to a stiff inner core.

In an embodiment only the distal most tip of the spike is relatively stiff with the mid and proximal portions of the spike being more compliant than the distal portion. This may allow more compatibility with the annulus and/or sewing ring to prevent laceration and resultant device instability.

In an embodiment barbs in the proximal portion of the spike may be less resilient than those in the distal portion of the spike considering the sewing ring (near proximal portion of deployed spike) is tougher and not subject to laceration issues like the more distal annulus. This may be most suitable for supraannular valve implant scenarios but the concept is applicable for other implant scenarios such that the portion of the spike likely to contact the sewing ring may have stiffer barbs than other portions of the spike that will contact tissue.

An embodiment includes barbs that oppose each other. For example, barbs on a proximal portion of the barbed rod may resist proximal movement (and engage the sewing ring by using barbs with an obtuse angle to a longitudinal axis of spike) and barbs on the distal portion of the barbed rod may resist distal movement (and engage the annulus by using barbs with an acute angle to a longitudinal axis of spike). An embodiment includes a non-circular cross section (e.g., triangular) for the spike.

As used herein "spike" or "barbed rod" or "rod" does not necessarily connote a stiff rod but may in fact include a compliant section or sections along its length.

An embodiment includes a kit including spikes and a valve with a sewing ring having designated areas for spike reception. The areas may include apertures, areas less dense than other areas of the sewing ring, and the like. Other embodiments work with sewing rings that are not modified in any manner from traditional sewing rings.

An embodiment includes pliable barbs that avoid laceration of tissue when the spike is pulled or pushed towards its proximal end.

While some embodiments include a blunt end and a sharpened end other embodiments include two opposite ends, both being sharpened.

Various embodiments of the invention are suitable for implantation intra-annularly, intrasupra-annularly, and supra-annularly.

An embodiment may include a variety of materials including polypropylene, PTFE, ePTFE, and nylon.

An embodiment includes a kit comprising a valve (including a sewing ring) and a plurality of spikes. In an embodiment the spikes vary in length, diameter, and shape (e.g., varying amounts of curve along body of spike). Some embodiments include a proximal head (see FIG. 1) while others do not.

An embodiment includes a barbed rod comprising: a rod having an blunt end and a sharpened end, a longitudinal axis, an exterior surface, and a plurality of barbs disposed along the exterior surface; with each barb being at least one of, rotationally displaced around the longitudinal axis of the rod and axially displaced along the longitudinal axis of the rod, relative to each adjacent barb. Each barb has a tip and a base with each base being defined by a cut into the exterior surface of the rod; wherein the cut has an angle relative to the longitudinal axis of the rod which changes between the tip of each barb and the base of each barb; and wherein the barbed rod is adapted for use in surgical applications to hold a valve sewing ring proximate to a valve annulus. In an embodiment the barbed rod includes a metallic core that is radiopaque. In an embodiment the core is a shape memory alloy. In an embodiment the shape memory alloy has a primary state that is curved (e.g., FIG. 4) and a linear shape when included in a deployment conduit.

An embodiment of the invention includes a method including situating a mechanical valve, having a sewing cuff, in a patient's aortic root and coupling the cuff along the surgical annulus using one or more spike embodiments while taking into account anatomical variances of the fibrous portions of the heart and/or other anatomical issues. The cuff may be coupled to the annulus along the thickened fibrous portions of the patient's fibrous crown-shaped annulus.

The following examples pertain to further embodiments.

Example 1 includes first and second conduits respectively including first and second barbed rods; and first and second shafts; wherein: (a)(i) in a first configuration the first shaft slides distally within the first conduit and couples to a proximal end of the first barbed rod, and (a)(ii) in a second configuration the first shaft slides distally within the first conduit and pushes the first barbed rod out of the first conduit; wherein: (a)(i) in an additional first configuration the second shaft slides distally within the second conduit and couples to a proximal end of the second barbed rod, and (a)(ii) in an additional second configuration the second shaft slides distally within the second conduit and pushes the second barbed rod out of the second conduit.

Figure 5:
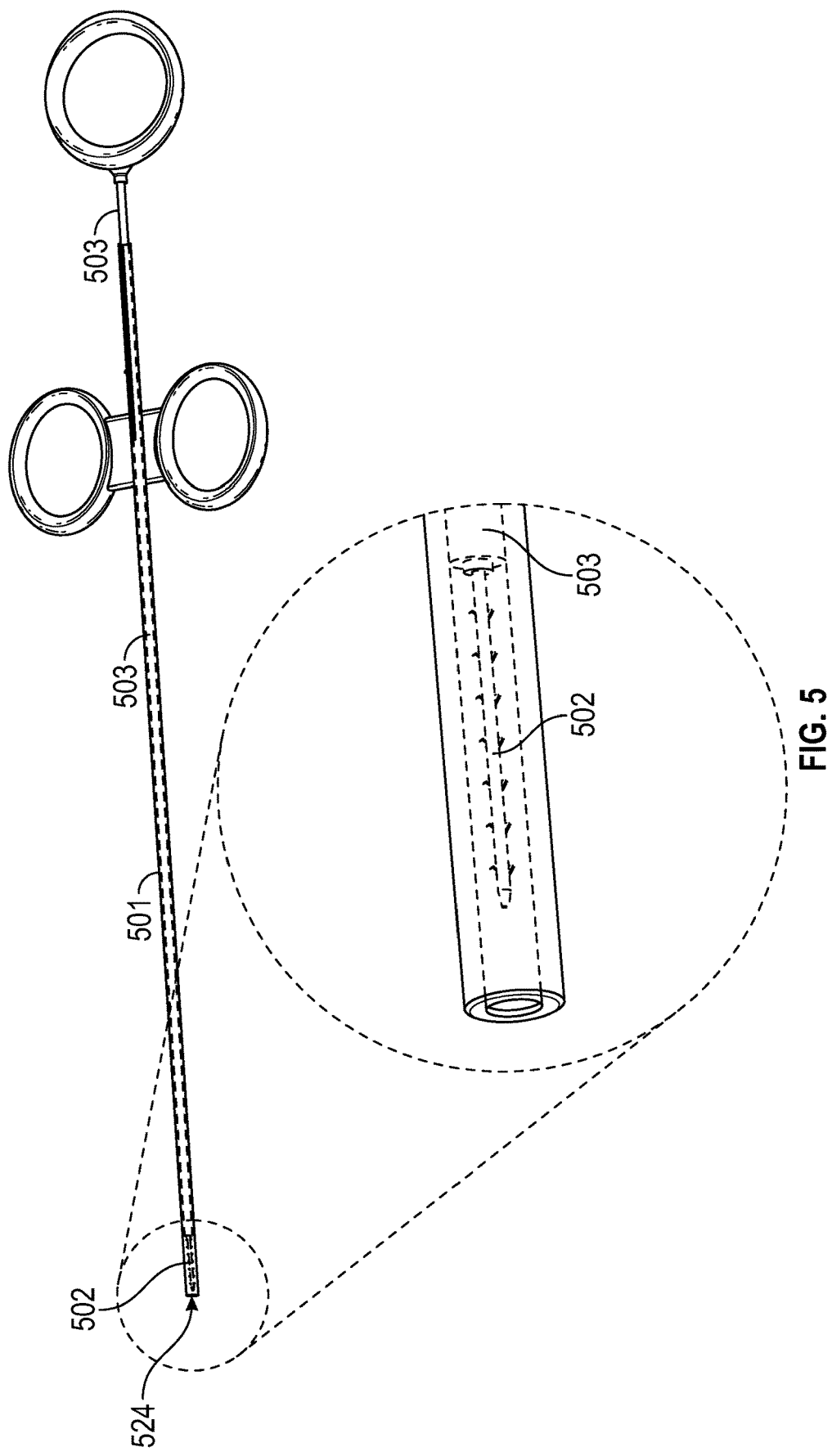
FIG. 5 depicts a prosthesis delivery system in an embodiment.
Figure 7A:
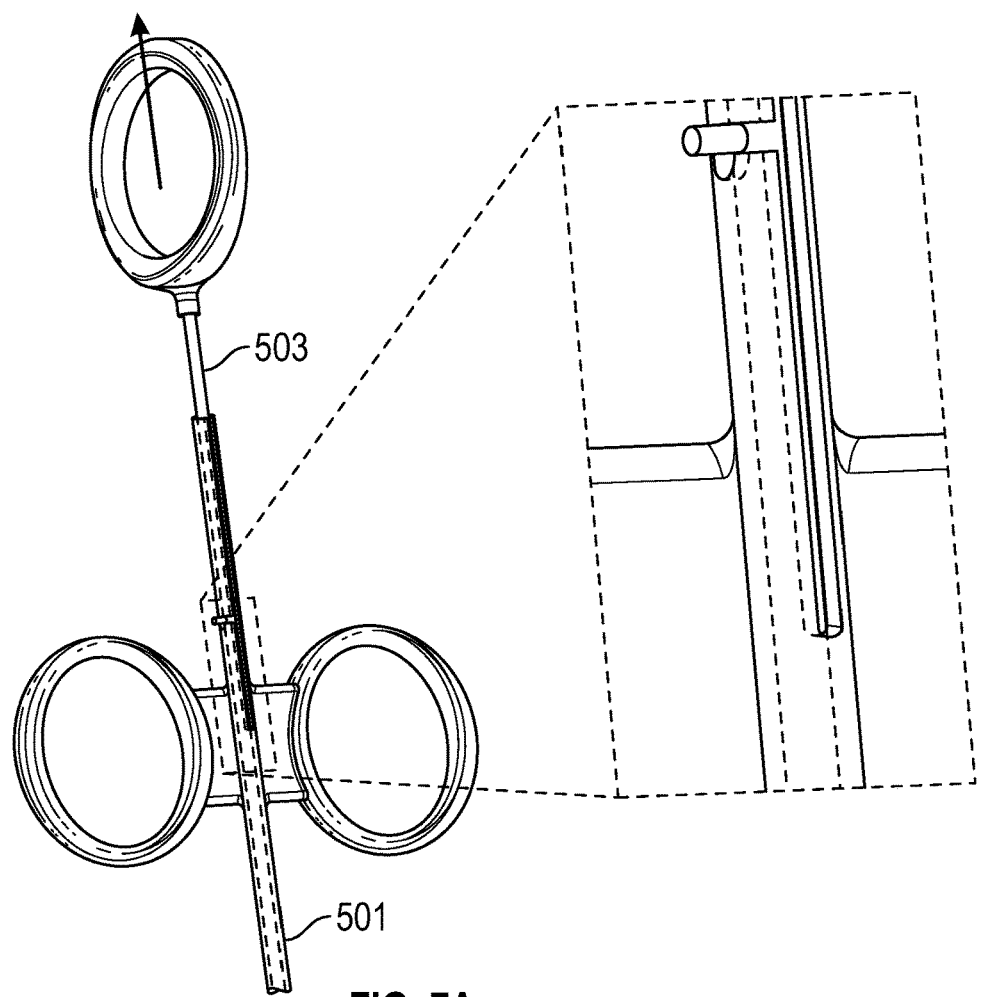
Figure 7B:
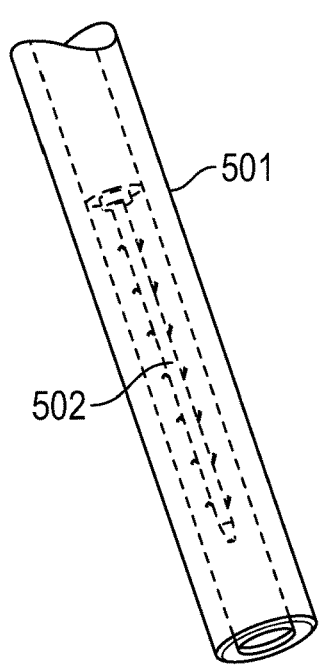
Figure 8A:
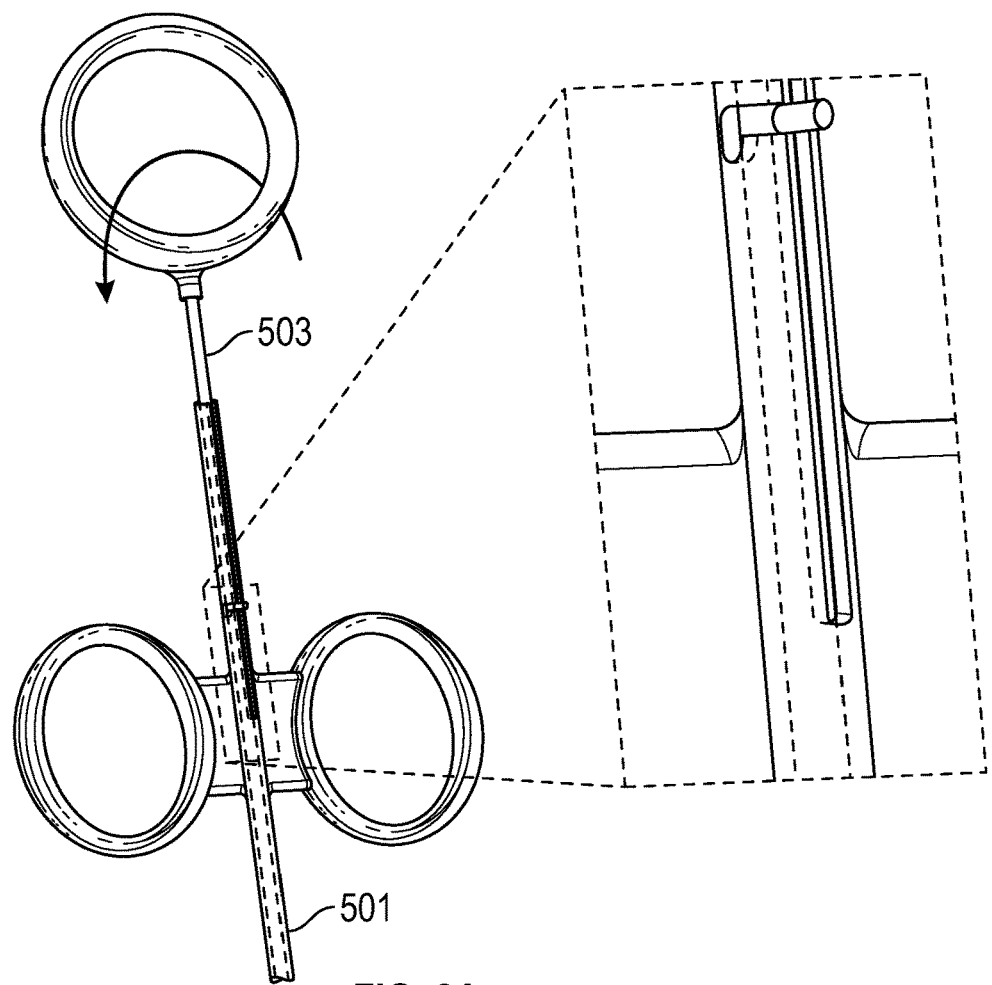
Figure 8B:
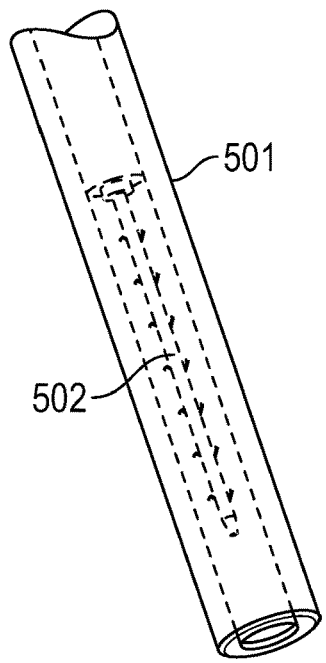
Figure 9A:
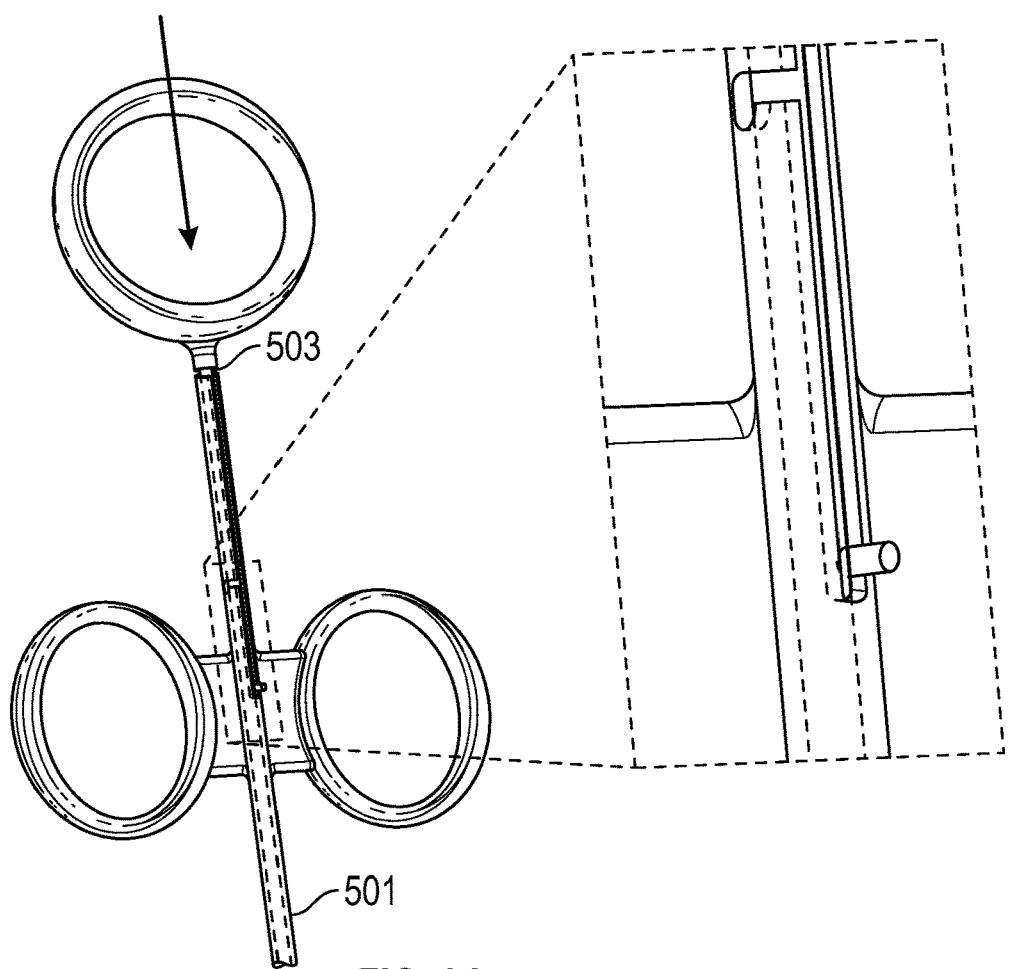
Figure 9B:
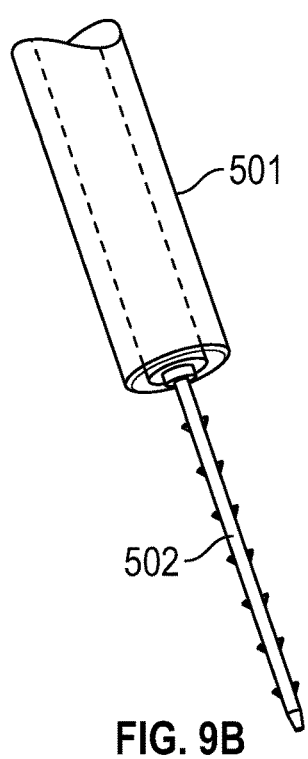
Figure 10A:
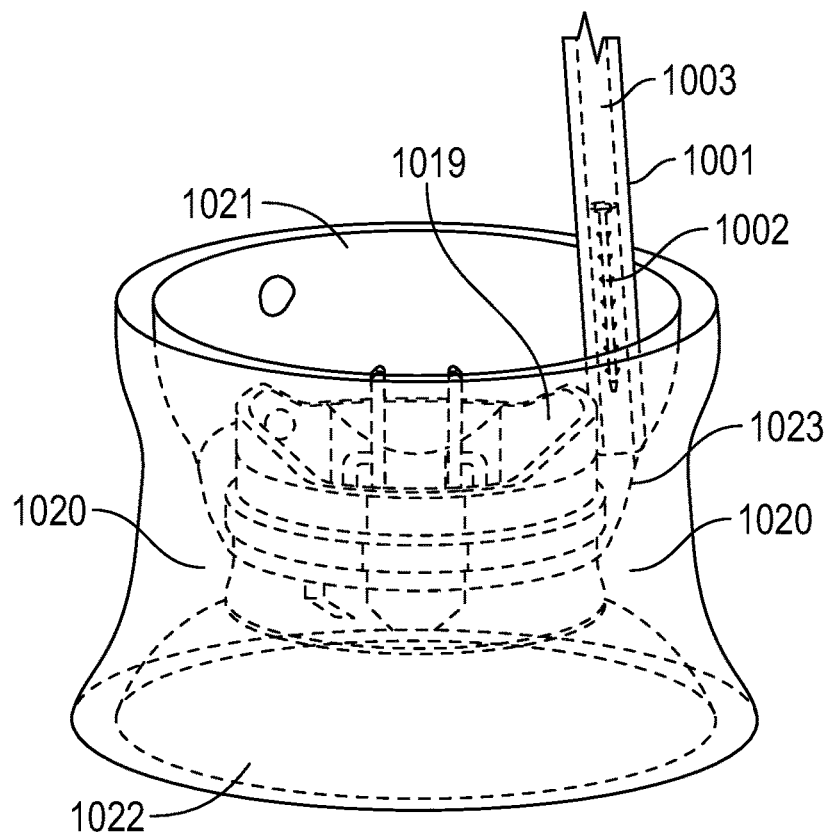
FIGS. 10a-10d depict a process of using a prosthesis delivery system in an embodiment.
Figure 10B:
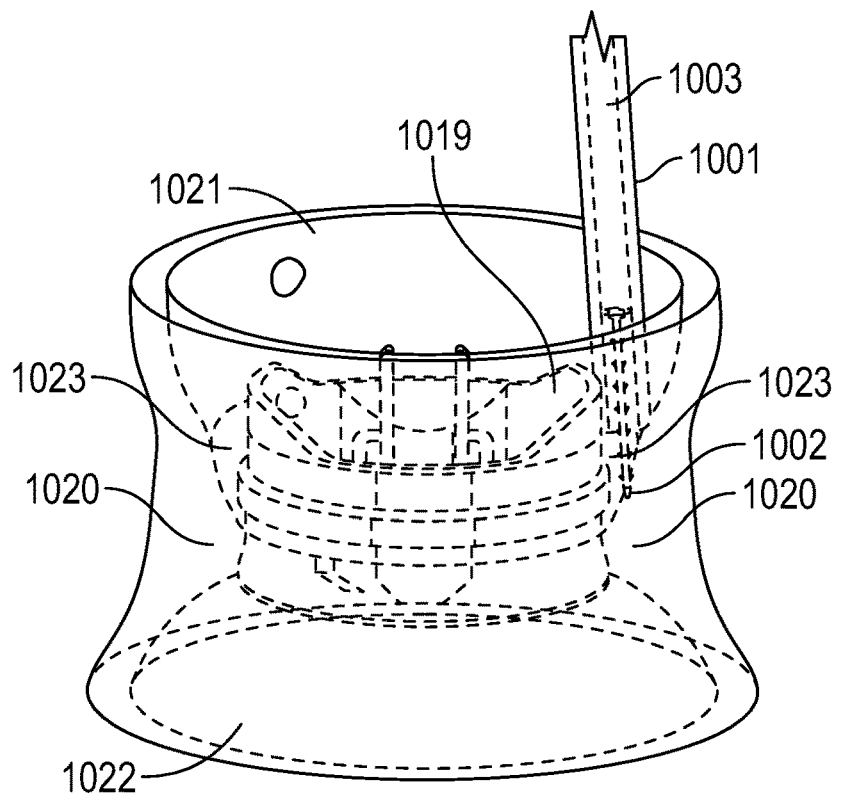
Figure 10C:
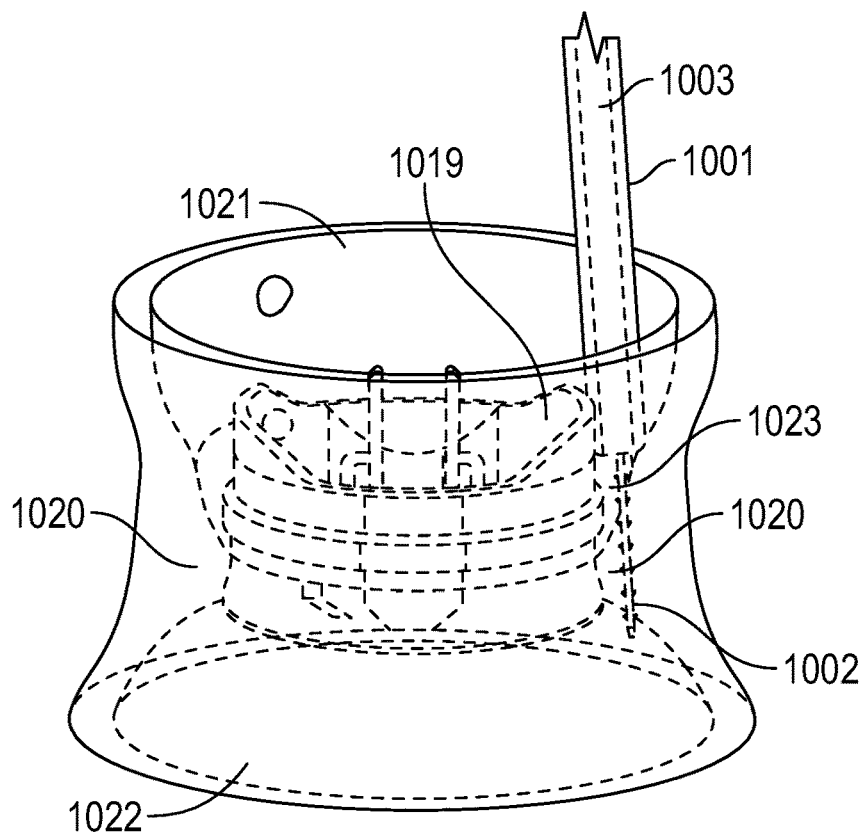
Figure 10D:
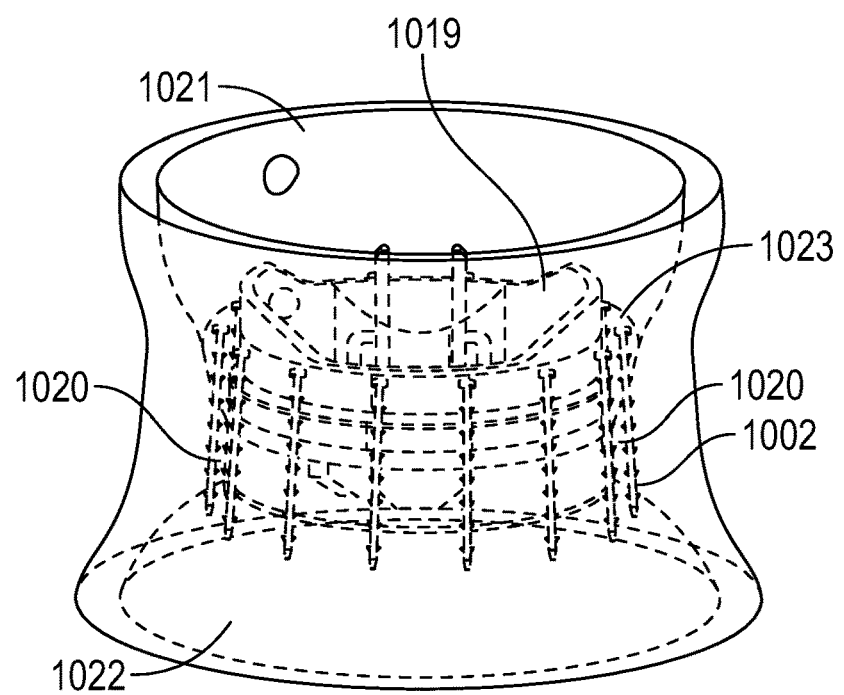

For instance, FIG. 5 includes one such conduit 501 but a kit may include an assortment of such conduits. Each conduit may be shipped with a barbed rod 502 already included within the conduit. Shaft 503 may be shipped already located within conduit 501 or may be inserted into the conduit once the kit is unpacked in the medical facility. As shown in FIGS. 6a-8b show an example of the first configuration where the shaft 503 has not yet pushed the rod 502 from the conduit 501. FIGS. 9a-9b show an example of the second configuration where the shaft 503 has ejected or pushed the rod 502 from the conduit 501.

Thus, FIG. 5 discloses a delivery device that is a single-use disposable system that is presented to the surgeon in a sterile ready-to-use state. One embodiment of the delivery device is a long syringe-style cannula with a concentric central shaft. The prosthesis spike is affixed to the distal end of the central shaft, which is secured within the cannula.

Figure 6A:
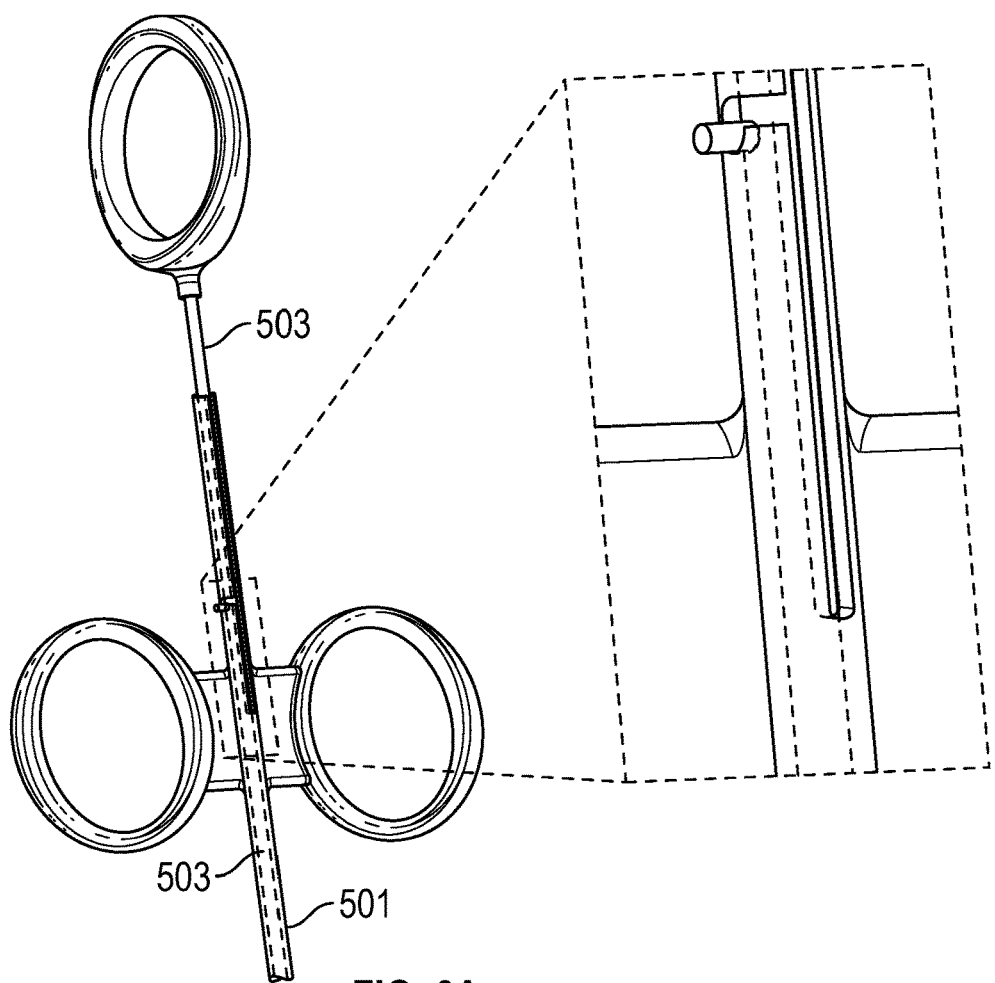
FIGS. 6a-6b, 7a-7b, 8a-8b, 9a-9b depict a process of using a prosthesis delivery system in an embodiment.
Figure 6B:
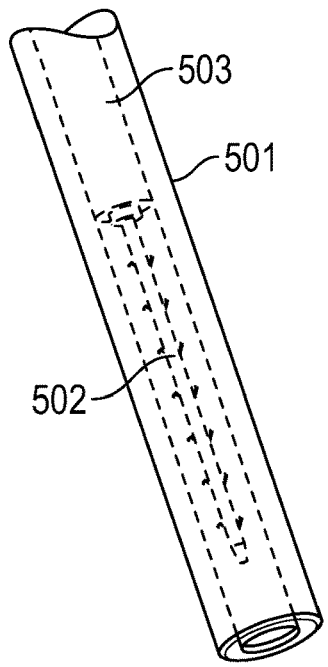

FIGS. 6a-6b disclose a sequence where the device is locked and shaft 503 cannot rotate nor advance. Prosthesis spike 502 is housed within cannula 501. FIGS. 7a-7b depict a situation where a surgeon slightly retracts the central shaft 503. Shaft 503 may now rotate but cannot advance. Prosthesis spike 502 is still is housed within cannula 501. FIGS. 8a-8b depict a situation where a surgeon rotates the central shaft 503 90°. Shaft 503 is now unlocked and is free to advance. Prosthesis spike 502 is housed within cannula 501. FIGS. 9a-9b depict when a surgeon advances the central shaft 503. Prosthesis spike 502 is deployed at the surgeon's discretion (force, speed, position, etc.).

Another version of example 1 includes first and second conduits respectively including first and second barbed rods; first and second shafts; wherein: (a)(i) in a first configuration the first shaft is configured to slide distally within the first conduit and couple to a proximal end of the first barbed rod, and (a)(ii) in a second configuration the first shaft is configured to slide distally within the first conduit and push the first barbed rod out of the first conduit; wherein: (a)(i) in an additional first configuration the second shaft is configured to slide distally within the second conduit and couple to a proximal end of the second barbed rod, and (a)(ii) in an additional second configuration the second shaft is configured to slide distally within the second conduit and push the second barbed rod out of the second conduit.

The shaft may couple to the rod directly or indirectly.

Example 2 includes the system of example 1, wherein: the proximal end of the first barbed rod is blunt and a distal end of the first barbed rod is sharpened; the first barbed rod includes a longitudinal axis, an exterior surface, and a plurality of barbs disposed along the exterior surface; each barb of the plurality of barbs is at least one of: (b)(i) rotationally displaced around the longitudinal axis of the rod, and (b)(ii) axially displaced along the longitudinal axis of the rod relative to each adjacent barb.

For example, in FIG. 1 rod 102 includes a blunted proximal end 104 and a sharpened distal end 105. By "end" reference made to the general portion near the terminus of the rod and is not mean to mean a distal most or proximal most face. The outer surface of rod 102 includes barbs 106. In FIG. 1, the barbs are axially displaced along the longitudinal axis 107 of the rod relative to each adjacent barb but are not rotationally displaced around the longitudinal axis of the rod. Rotationally displacement would yield a corkscrew or helical pattern of barbs, which is present in various embodiments.

Example 3 includes the system of example 1, wherein the first barbed rod includes a radiopaque core.

For example, FIGS. 2a-2b include core 210. Core 210 may be radiopaque because it includes a metal (titanium, stainless steel, nickel alloy, shape memory alloy (e.g., Nitinol), and the like. The core may be stiff or flexible or may have varying stiffness along its length. FIGS. 2a-2b depict an embodiment featuring a metallic (e.g., Nitinol, Stainless Steel, Iridium) core for added rigidity of the construct. Furthermore, this metallic core is visible during radiographic imaging to assist in initial placement of the barb and valve, or to confirm placement at a later examination of the patient (e.g., human, dog, animal).

Example 4 includes the system of example 3, wherein the core includes at least one of a metal and a shape memory alloy.

Example 5 includes the system of example 4, wherein the core is monolithic and extends from a proximal third of the first barbed rod to a distal third of the first barbed rod.

For example, in FIG. 2a core 210 extends from proximal third 211, through middle third 212, to distal third 213. By "monolithic" the core may be, for example, stamped or extruded or otherwise formed as a single piece and is not coupled together with welds, adhesives, or joints.

Figure 3B:
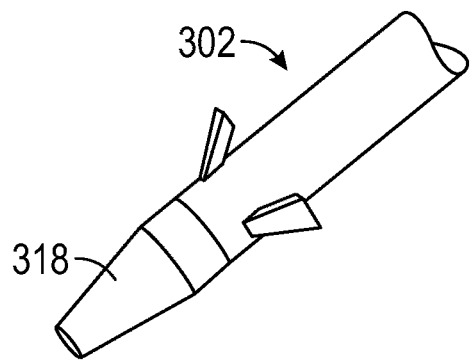

FIGS. 3a-3b provide an instance whereby a reinforced distal end 318 is hardened and may include a metal or polymer to reinforce the distal end of barbed rod 302 and facilitate penetration of the rod into tough cardiac tissue (e.g., valve annulus).

Example 6 includes the system of example 4, wherein the first barbed rod includes an outer layer around the core, the outer layer having a first hardness and the core having a second hardness that is harder than the first hardness.

For instance, FIG. 2a shows outer layer 214 which may include polypropylene, polytetrafluoroethylene (PTFE), expanded PTFE (ePTFE), and/or nylon (although this is a non-exhaustive list). A metal core would be harder than a PTFE outer layer.

Hardness is a characteristic of a material. It is defined as the resistance to indentation, and it is determined by measuring the depth of the indentation. More simply put, when using a fixed force (load) and a given indenter, the smaller the indentation, the harder the material. The Rockwell hardness test method, as defined in ASTM E-18, is one option for testing hardness.

Example 7 includes the system of example 6, wherein the outer layer includes a material selected from the group comprising: polypropylene, polytetrafluoroethylene (PTFE), expanded PTFE (ePTFE), and nylon.

Other embodiments are not limited to these materials.

Example 8 includes the system of example 7, wherein the first barbed rod includes a plurality of barbs that include the material.

For instance, in an embodiment barbs 206 are formed from the outer layer material. They may be molded, extruded, or simply cut from outer layer 214.

Example 9 includes the system of example 7, wherein the core includes at least one aperture and the outer layer passes from one side of the first barbed rod to another side of the first barbed rod via the at least one aperture.

For instance, in FIG. 2a aperture 215 passes through core 210. Aperture 215 is purely optional and is not included in all embodiments. Aperture 215 may be reproduced and found in other locations along core 210.

Example 10 includes the system of example 9, wherein: the outer layer includes a first portion that contacts the one side of the first barbed rod, a second portion included in the at least one aperture, and a third portion that contacts the another side of the first barbed rod; and the first, second, and third portions are monolithic with each other.

For instance, in FIG. 2a outside layer portions 216 and 217 join one another through aperture 215. Doing so may help keep outer layer 214 in place and prevent sliding of core 210 with relation to outside layer 214. Thus, to ensure the outer covering or layer 214 does not "ride up" the inner rod during insertion of the spike, in an embodiment the inner rod includes one or more apertures through which the outer layer penetrates, thereby creating a situation where the outer later on a right side of the inner rod is formed through apertures in the inner rod (spread linearly up the long axis of the inner rod) and joins the outer layer on the left side of the rod. The left and right sides, along with the portions traversing the apertures, may be monolithic with one another. One of the apertures may be located near the distal end of the spike to counter shear forces that concentrate near the distal end of the inner rod upon insertion into the sewing ring and/or tissue.

As addressed above, "the outer layer includes a first portion that contacts the one side of the first barbed rod" does not necessarily mean the contact is a direct contact and, for example, an intermediate layer may be between the core and the outer layer.

Example 11 includes the system of example 6, wherein the first barbed rod includes a distal end having a first stiffness and the proximal end of the first barbed rod has a second stiffness unequal to the first stiffness.

For example, in FIG. 2a portion 213 may be stiffer than portions 212 and/or 211. In another embodiment, portion 211 may be stiffer than portions 213 and/or 211. Stiffness is the resistance of a body to deflection or deformation by an applied force and can be expressed as $k=F/\delta$, where $k$=stiffness (N/m, lb/in), $F$=applied force (N, lb), and $\delta$=extension (m, in).

Example 12 includes the system of example 11, wherein the second stiffness is stiffer than the first stiffness.

Example 13 includes the system of example 11, the distal end of the first barbed rod has a first plurality of barbs each having a first additional stiffness and the proximal end of the first barbed rod has a second plurality of barbs each having a second additional stiffness unequal to the first additional stiffness.

For instance, the barbs located in area 213 may be stiffer than the barbs located in areas 212 and/or 211. In another embodiment, the barbs located in area 211 may be stiffer than the barbs located in areas 212 and/or 213.

Example 14 includes the system of example 6 comprising a heart prosthetic including a sewing cuff, wherein: the prosthetic includes a member selected from the group comprising a heart valve and an annuloplasty ring; and the sewing cuff includes a radial cross-sectional diameter and the first barbed rod includes a diameter that is less than the radial cross-sectional diameter.

Example 15 includes the system of example 5, wherein the core is arcuate.

Figure 4:
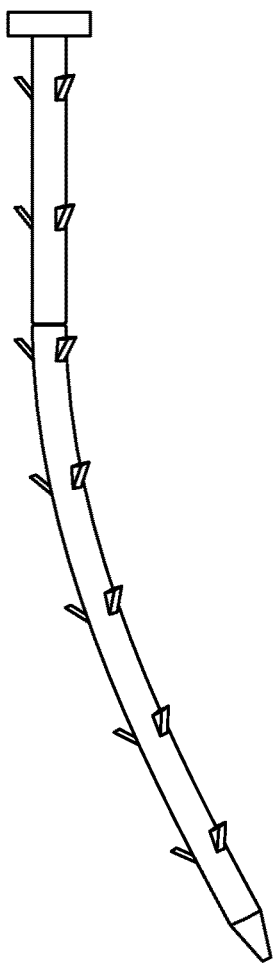
FIG. 4 depicts a prosthesis in an embodiment.

For example, FIG. 4 shows such an arcuate nature. The arcuate nature may be fixed (e.g., when the core is composed primarily of titanium). The arcuate nature may be the set or programmed shape for a shape memory alloy that contrasts with a secondary linear shape when the spike is located within a delivery conduit such as conduit 501 of FIG. 5. Thus, FIG. 4 shows an embodiment wholly or partially curved such that it matches the anatomical interface between a native valve annulus and a mechanical valve sewing ring. This embodiment allows the clinician better access to challenging patient anatomy in the event of a minimally invasive surgical approach (e.g., via transcatheter access or via keyhole surgery via a space between a patient's ribs). For example, with a transcatheter access approach the barbed rod may be deployed via a catheter. The catheter and/or sheath may constitute the "conduit" described herein (e.g., conduit 501) and a pusher rod (similar to a guide wire) may constitute the shaft (e.g., shaft 503) described herein. The pusher rod may include Nitinol or other material(s) that are flexible enough to navigate vasculature yet stiff enough to transfer force from a physician to a barbed spike.

If the core is fixed in an arcuate form, the corresponding conduit may be arcuate as well. For example, a distal most portion of the conduit may be arcuate and include the barbed rod. The more proximal portions of the conduit may be linear and non-arcuate.

Example 16 includes the system of example 5, wherein the proximal end of the first barbed rod has a first diameter and a middle shaft portion of the first barbed rod has a second dimeter that is less than the first diameter.

For example, in FIG. 1 diameter 108 is greater than diameter 109.

Example 17 includes a method comprising: providing first and second conduits, respectively including first and second barbed rods, and first and second shafts; locating a prosthetic, having a sewing cuff, in a patient; sliding the first shaft distally within the first conduit and, in response to sliding the first shaft, forcing the first barbed rod through the sewing cuff and into cardiac tissue of the patient to secure the prosthetic to the cardiac tissue; sliding the second shaft distally within the second conduit and, in response to sliding the second shaft, forcing the second barbed rod through the sewing cuff and into cardiac tissue of the patient to secure the prosthetic to the cardiac tissue.

For instance, FIGS. 10a-10d include an embodiment. The valve annulus 1020 is prepared as with any mechanical valve replacement, and a mechanical valve 1019 is positioned between ascending aorta 1021 and left ventricle 1022. The brand and size of the mechanical valve prosthesis is irrelevant for some embodiments, and the technique of example 17 is suitable for, as an example, either aortic or mitral applications (i.e., may be used with artificial or biological valves (also called tissue valves) for any valve including aortic or mitral valves).

The surgeon selects the prosthesis spike to be implanted. An embodiment includes a kit having a variety of prosthesis configurations to accommodate differing patient anatomy and surgeon preference, with options varying based on some or all of the following parameters: rod length, rod diameter, and material included in the rod/spike. The delivery device is positioned onto the sewing ring 1023 of the replacement valve. Then the surgeon actuates the delivery device (e.g., conduit 1001 and shaft 1003) to deploy a spike prosthesis 1002 (FIGS. 10b and 10c) into the sewing ring 1023 and valve annulus 1020. The surgeon has direct tactile control of the applied force, speed, and position of the prosthesis spike.

In an embodiment, the surgeon removes the delivery device (e.g., conduit 1001 and shaft 1003) and discards the device. The prosthesis spike remains intact and secures the valve to the valve annulus (through the sewing ring/sewing cuff). The one-directional barbs on the prosthesis spike prevent device back-out, while the spike head (e.g., head in region 104 of FIG. 1) prevents the prosthesis from advancing further (i.e., advancing too far).

The surgeon selects and implants additional prosthesis spikes (e.g., FIG. 10d) in order to fully secure the valve. The surgeon may vary the prosthesis spikes (e.g., diameter, length, material, and angle) about a single valve to suit a particular patient anatomy or surgical preference. The surgeon may use multiple spikes possibly in cooperation with some traditional and/or barbed suture.

Example 18 includes the method of example 17, wherein forcing the first and second barbed rods through the sewing cuff and into the cardiac tissue comprises forcing the first and second barbed rods through the sewing cuff and into an anatomic annulus portion of the cardiac tissue.

Example 19 includes the method of example 18, comprising directly contacting the first shaft to the sewing cuff before forcing the first barbed rod through the sewing cuff.

Example 20 includes a system comprising: a barbed rod that includes a radiopaque core; an outer layer around the core; wherein (a) the core includes at least one of a metal and a shape memory alloy, (b) the core is monolithic and extends from a proximal third of the barbed rod to a distal third of the barbed rod, (c) the outer layer has a first hardness and the core has a second hardness that is harder than the first hardness, and (d) the outer layer includes a material selected from the group comprising: polypropylene, polytetrafluoroethylene (PTFE), expanded PTFE (ePTFE), and nylon.

Thus, some embodiments do not include a delivery mechanism such as a conduit and shaft that slides within the conduit.

Example 21 includes the system of example 20, wherein the barbed rod includes a distal end having a first stiffness and a proximal end having a second stiffness unequal to the first stiffness.

Another version of example 21 includes the system of example 20, wherein the barbed rod includes a first portion having a first stiffness and a second portion having a second stiffness unequal to the first stiffness.

Another version of example 21 includes wherein the barbed rod includes a distal portion having a first stiffness and a proximal portion having a second stiffness unequal to the first stiffness.

Example 22 includes the system of example 21, wherein the core is arcuate.

Various embodiments of the spike prosthesis may vary in terms of the (a) the material included in the prosthesis, (b) the overall length of the prosthesis, (c) the diameter of the prosthesis, (d) the barb geometry the prosthesis, and/or (e) the barb density and spacing of the prosthesis. An embodiment includes a kit that offers the surgeon a set of these prosthesis from which s/he can choose the appropriate configuration to best suit the unique patient anatomy and surgical procedure.

In an embodiment a spike is formed with barbed suture by melting/forming the proximal end if the suture into a button or head, while the distal end is sharpened or cut on an angle forming a sharp point.

An embodiment modifies the embodiment of FIG. 5 and instead includes a sharpened delivery conduit. Specifically, the delivery conduit is sharpened at its distal end 524 and is used to penetrate the sewing ring and annulus. Thus, the distal tip of the delivery conduit (upon full insertion) traverses the sewing ring and some or all of the annulus. The barbed spike (with or without an inner support rod) is located near the distal tip of the insertion conduit. The barbed spike may be located near the distal tip of the insertion conduit after the conduit traverses the sewing ring and annulus or before that occurs. A plunger may then eject the barbed spike from the conduit so that a small portion of the spike (e.g., only one half of area 213 of FIG. 2a) is ejected from the distal end of the conduit. This small traverse length may help ease deployment of the barbed rod. The small portion may be barbed (e.g., see barbs 206') such that it takes purchase of tissue. As a result, no more deployment via the plunger is necessary—only the conduit needs to be withdrawn allowing the barbs 206' to purchase tissue and/or sewing ring. In such an embodiment the distal tip of the barbed spike may or may not be sharpened. Further, in such an embodiment the spike may or may not be rigid considering the delivery conduit engages the majority of implantation resistance so the spike does not have to.

In an embodiment a sharpened tip of the spike has a flange or lip that the delivery conduit (e.g., conduit 501) and/or pushing shaft (e.g., shaft 503) abuts such that the conduit need not be sharpened because the sharpened tip of the spike does the penetration work (e.g., through a sewing cuff and/or annulus). For example, in FIG. 3a dashed lines show an embodiment whereby a conduit 301' abuts a flange or lip formed by barbs 306" (however, a flange formed from something other than barbs may still suffice as long as it provides a surface for which the conduit may exert force upon). In an embodiment the distal head of the spike may have a flange or lip (similar to an arrow head) that the shaft (instead of outer conduit) may leverage to deploy the device into the sewing ring. In embodiments where the barbed rod has a distal flange the conduit need only be withdrawn once the spike is in place. As the conduit is withdrawn spikes are exposed and gain purchase in the sewing ring and/or annulus. Again, in such an embodiment the spike need not be rigid considering it is supported during implant by the conduit and the force is directed along the distal flange. If the conduit is used to force the spike forward the conduit may advance through the sewing ring and into the annulus. A pusher rod (e.g., shaft 503) may not be required in such an embodiment.

There are several different delivery devices including, for example, the system shown in FIG. 5. However, other systems may use, for example, a staple gun (mechanically actuated), or a nail gun (mechanical or air pressure actuated) that include a cartridge of spikes or barbed rods discussed herein.

An embodiment anchors a mechanical prosthetic heart valve into the remaining valve annulus of a patient. However, an embodiment anchors other prostheses to soft tissue (for example, an annuloplasty ring). An embodiment is for general wound closure and is not restricted to cardiac applications.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A system comprising:
first and second conduits respectively including first and second barbed rods; and
first and second shafts;
wherein: (a) in a first configuration the first shaft slides distally within the first conduit and couples to a proximal end of the first barbed rod, (b) in a second configuration the first shaft slides distally within the first conduit and pushes the first barbed rod out of the first conduit, (c) in an additional first configuration the second shaft slides distally within the second conduit and couples to a proximal end of the second barbed rod, and (d) in an additional second configuration the second shaft slides distally within the second conduit and pushes the second barbed rod out of the second conduit;
wherein the first barbed rod includes: (a) a radiopaque core, and (b) an outer layer around the core;
wherein (a) the outer layer includes a plurality of barbs and the core does not include the plurality of barbs; (b) the plurality of barbs includes first and second pluralities of barbs, (c) a distal end of the first barbed rod has the first plurality of barbs each having a first stiffness, (d) the proximal end of the first barbed rod has the second plurality of barbs each having a second stiffness unequal to the first stiffness, and (e) the first and second pluralities of barbs slope away from the core and toward a direction that is proximal or distal.

2. The system of claim 1, wherein:
the proximal end of the first barbed rod is blunt and the distal end of the first barbed rod is sharpened;
the first barbed rod includes a longitudinal axis and an exterior surface;
each barb of the plurality of barbs is at least one of rotationally displaced around the longitudinal axis of the first barbed rod, axially displaced along the longitudinal axis of the first barbed rod relative to each adjacent barb, or combinations thereof.

3. The system of claim 1, wherein the core includes at least one of a metal, a shape memory alloy, or combinations thereof.

4. The system of claim 3, wherein the core is monolithic and extends from a proximal third of the first barbed rod to a distal third of the first barbed rod.

5. The system of claim 4, wherein the core is arcuate over a majority of its length.

6. The system of claim 4, wherein the proximal end of the first barbed rod has a first diameter and a middle shaft portion of the first barbed rod has a second dimeter that is less than the first diameter.

7. The system of claim 3, wherein the outer layer has a first hardness and the core has a second hardness that is harder than the first hardness.

8. The system of claim 7, wherein the core includes: (a) a non-barbed distal end portion having an additional first stiffness, and (b) a non-barbed proximal end portion having an additional second stiffness unequal to the additional first stiffness.

9. The system of claim 7, comprising a heart prosthetic including a sewing cuff, wherein:
the heart prosthetic includes at least one of a heart valve, an annuloplasty ring, or combinations thereof; and
the sewing cuff includes a radial cross-sectional diameter and the first barbed rod includes a diameter that is less than the radial cross-sectional diameter.

10. The system of claim 7, wherein the outer layer includes at least one of polypropylene, polytetrafluoroethylene (PTFE), expanded PTFE (ePTFE), nylon, or combinations thereof.

11. The system of claim 10, wherein the core includes at least one aperture and the outer layer passes from one side of the first barbed rod to another side of the first barbed rod via the at least one aperture.

12. The system of claim 11, wherein:
the outer layer includes a first portion that contacts the one side of the first barbed rod, a second portion included in the at least one aperture, and a third portion that contacts the another side of the first barbed rod; and
the first, second, and third portions are monolithic with each other.

13. The system of claim 1, wherein a distal-most tip of the core extends distal to a distal-most tip of the outer layer.

14. The system of claim 1, wherein the first conduit includes a sharpened distal tip.

15. A system comprising:
first and second conduits respectively including first and second barbed rods; and
first and second shafts;
wherein: (a) in a first configuration the first shaft slides distally within the first conduit and couples to a proximal end of the first barbed rod, and (b) in a second configuration the first shaft slides distally within the first conduit and pushes the first barbed rod out of the first conduit; (c) in an additional first configuration the second shaft slides distally within the second conduit and couples to a proximal end of the second barbed rod, and (d) in an additional second configuration the second shaft slides distally within the second conduit and pushes the second barbed rod out of the second conduit;
wherein the first barbed rod includes: (a) a radiopaque core, and (b) an outer layer around the core;
wherein (a) the outer layer includes a plurality of barbs and the core does not include the plurality of barbs, and (b) a distal-most tip of the core extends distal to a distal-most tip of the outer layer.

16. The system of claim 15, wherein:
the proximal end of the first barbed rod is blunt and a distal end of the first barbed rod is sharpened;
the first barbed rod includes a longitudinal axis and an exterior surface;
each barb of the plurality of barbs is at least one of rotationally displaced around the longitudinal axis of the first barbed rod, axially displaced along the longitudinal axis of the first barbed rod relative to each adjacent barb, or combinations thereof.

17. The system of claim 15, wherein the core is monolithic and extends from a proximal third of the first barbed rod to a distal third of the first barbed rod.

18. The system of claim 15, wherein, the outer layer has a first hardness and the core has a second hardness that is harder than the first hardness.

19. The system of claim 18, wherein the outer layer includes at least one of polypropylene, polytetrafluoroethylene (PTFE), expanded PTFE (ePTFE), nylon, or combinations thereof.

20. The system of claim 18, comprising a heart prosthetic including a sewing cuff, wherein:
the heart prosthetic includes at least one of a heart valve, an annuloplasty ring, or combinations thereof; and
the sewing cuff includes a radial cross-sectional diameter and the first barbed rod includes a diameter that is less than the radial cross-sectional diameter.

21. The system of claim 15, wherein the core includes at least one aperture and the outer layer passes from one side of the first barbed rod to another side of the first barbed rod via the at least one aperture.

22. The system of claim 15, wherein the core includes: (a) a non-barbed distal end portion having a first stiffness, and (b) a non-barbed proximal end portion having a second stiffness unequal to the first stiffness.

* * * * *